US00PP10925P

United States Patent [19]

Meier et al.

[11] Patent Number: Plant 10,925

[45] Date of Patent: May 25, 1999

[54] KENTUCKY BLUEGRASS, NAMED 'BA74-17'

[75] Inventors: Virgil D. Meier, Marysville, Ohio; Jay B. Burr, Salem, Oreg.

[73] Assignee: OMS Investments, Inc., Wilmington, Del.

[21] Appl. No.: 08/949,938

[22] Filed: Oct. 14, 1997

[51] Int. Cl.[6] ..... A01H 5/00

[52] U.S. Cl. ..... Plt./90.2

[58] Field of Search ..... Plt./90.2

[56] References Cited

U.S. PATENT DOCUMENTS

| | | | |
|---|---|---|---|
| P.P. 3,156 | 5/1972 | Fuchigami et al. | Plt./88 |
| P.P. 3,186 | 5/1972 | Barenbrug et al. | Plt./88 |
| P.P. 4,336 | 11/1978 | Mayer et al. | Plt./88 |
| P.P. 6,280 | 9/1988 | Meier et al. | Plt./88 |
| P.P. 6,537 | 1/1989 | Meier et al. | Plt./88 |
| P.P. 6,538 | 1/1989 | Meier et al. | Plt./88 |
| P.P. 6,585 | 2/1989 | Meier et al. | Plt./88 |
| P.P. 7,831 | 3/1992 | Meier et al. | Plt./88 |
| P.P. 8,490 | 12/1993 | Meier et al. | Plt./90.2 |
| P.P. 9,036 | 1/1995 | Meier et al. | Plt./90.2 |
| P.P. 9,209 | 7/1995 | Meier et al. | Plt./90.2 |
| P.P. 9,611 | 7/1996 | Meier | Plt./90.2 |
| P.P. 9,848 | 4/1997 | Meier et al. | Plt./90.2 |
| P.P. 9,977 | 7/1997 | Meier et al. | Plt./90.2 |

*Primary Examiner*—Elizabeth Kemmerer

*Attorney, Agent, or Firm*—Jones, Day, Reavis & Pogue

[57] ABSTRACT

A variety of Kentucky Bluegrass having a medium to high level of resistance to leaf spot and melting out, leaf rust, Fusarium patch and red thread; a dark green color throughout the growing season; the ability to form a medium to high quality turf under a variety of environmental conditions; short growth and a high seed yielding capacity.

1 Drawing Sheet

FIELD OF THE INVENTION

The present invention relates to a new and distinct variety of *Poa pratensis* that has been designated Ba74-17 Kentucky Bluegrass.

DESCRIPTION OF RELATED ART

Kentucky Bluegrass have been disclosed in U.S. Plant Pat. No. 3,156, issued May 9, 1972; U.S. Plant Pat. No. 3,186, issued May 23, 1972; U.S. Plant Pat. No. 4,336, issued Nov. 28, 1978; U.S. Plant Pat. No. 6,280, issued Sep. 6, 1988; U.S. Plant Pat. Nos. 6,537 and 6,538, issued on Jan. 17, 1989; U.S. Plant Pat. No. 6,585, issued Feb. 7, 1989; U.S. Plant Pat. No. 7,831, issued Mar. 17, 1992; U.S. Plant Pat. No. 8,490, issued Dec. 7, 1993; U.S. Plant Pat. No. 9,036, issued Jan. 3, 1995; U.S. Plant Pat. No. 9,209, issued Jul. 18, 1995; U.S. Plant Pat. No. 9,611, issued Jul. 23, 1996; U.S. Plant Pat. No. 9,848, issued Apr. 1, 1997; U.S. Plant Pat. No. 9,977, issued Jul. 22, 1997; pending U.S. Plant patent application Ser. No. 08/680,168, filed Jul. 15, 1997; pending U.S. Plant patent application Ser. No. 08/680,167, filed Jul. 15, 1997; pending U.S. Plant patent application Ser. No. 08/763,076, filed Dec. 10, 1996.

SUMMARY OF THE VARIETY

The present invention relates to a new and distinct variety of *Poa pratensis* that has been designated Ba74-17 Kentucky Bluegrass.

Ba74-17 plant material was selected from the open pollinated progeny of PI-1369718, a Kentucky Bluegrass plant grown and maintained in a Breeders Nursey at The Scott Company's Research Station in Marysville, Ohio. After testing and observing the Ba74-17 Kentucky Bluegrass variety, it was determined to be a distinct variety, and it was asexually propagated by rhizomes, tillers and disseminules. Seed of Ba74-17 Kentucky Bluegrass was produced first at Marysville, Ohio and later at Gervais, Oreg. This seed was used to plant turf performance evaluation trials and later seed production fields.

In field and laboratory tests, it was demonstrated that Ba74-17 was significantly different at the 0.05% level from its female parent, PI-1369718, on the basis of the following characteristics: culm length, panicle length, seed weight, and leaf spot incidence. A comparison of the two grasses is given in the following table:

| | Mean Values | | | |
|---|---|---|---|---|
| Variety | Culm Length (cm) | Panicle Length (cm) | Seed weight (gms) | Leaf spot Incidence* |
| Ba74-17 | 33.6 | 7.7 | 0.26 | 7.8 |
| PI 1369718 | 30.0 | 7.2 | 0.21 | 8.2 |

*Leaf spot incidence rated 0–9, 9 = most leaf spot disease

Asexual production of Ba 74-17 by propagules (tillers and rhizomes) and by disseminules (modified caryopses produced by apomixis) has consistantly produced progeny plants indistinguishable from a mother plant Ba 74-17 in regard to characteristics other than those specified above. The apomixis level of Ba74-17 is approximately 95% based upon examining seedling characteristics of approximately 100 to 150 seedlings from different crop years in a growth chamber.

Ba74-17 has a number of highly desirable characteristics including a medium to high level of resistance to Drechslera spp. that causes leaf spot, melting out and crown rot, Puccinia spp. that causes rust infection such as leaf rust, Fusarium spp. that causes Fusarium patch and *Laetisaria fuciformis* that causes red thread. Ba74-17 is an overall good turfgrass performer as evidenced by medium to high scores for quality and color. Ba74-17 has a high seed yield potential in the Bluegrass seed production region of the northwestern U.S.A.

In comparison with a number of other Kentucky Bluegrass varieties, Ba74-17 is slightly above average in seed length and width, and rachilla length and has an average amount of lemma hairs. The panicle is below average in length and width, above average in whorl number, and above average branch count for both the lower and third whorls. Ba74-17 has below average size spikelets, a significantly lower number of florets and shorter glumes. The peduncle is below average in length and above average width, and significantly shorter culm length, below average in node number and internode length. The flag leaf is of average length, width and thickness. The flag leaf ligule is above average in length, has an average amount of hair on the dorsal side of the ligule but below average hair content on the leaf margin. The vegetative leaf is of average length and thickness but the leaf width is significantly narrower and the ligule is below average in length. The hair content of the vegetative leaf is above average for the upper margin of the ligule, and is significantly less on the leaf margin.

DETAILED DESCRIPTION OF THE VARIETY

Figure 1:
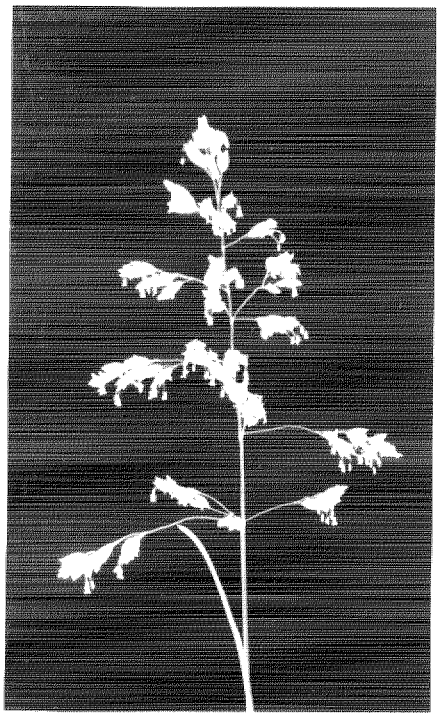
FIG. 1 is a Ba74-17 Kentucky Bluegrass panicle during anthesis.
Figure 3:
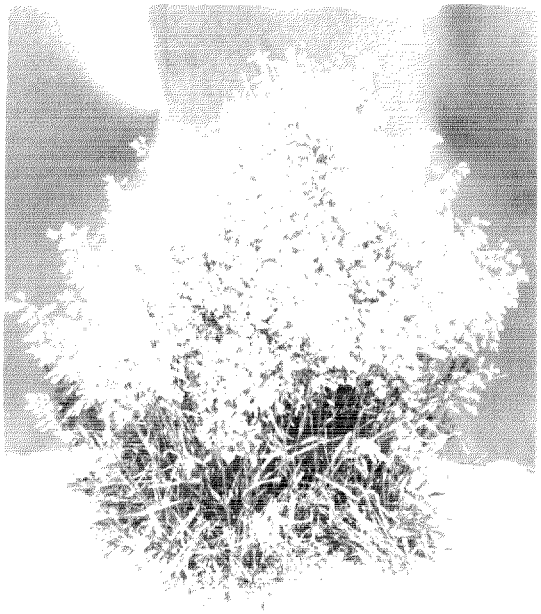
FIG. 3 is a Ba74-17 Kentucky Bluegrass plant shortly after completing anthesis.
Figure 2:
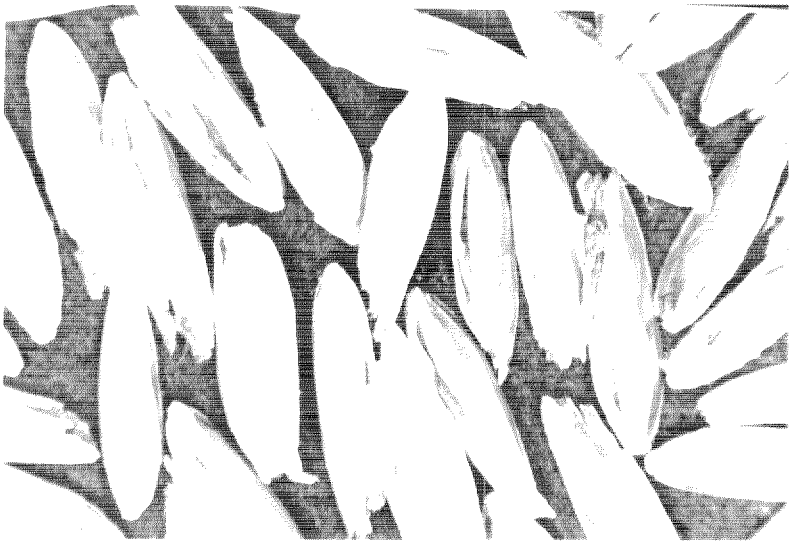
FIG. 2 is a Ba74-17 Kentucky Bluegrass seed.

Ba74-17 Kentucky Bluegrass (*Poa pratensis* L.) is perennial with creeping rhizomes forming a dense turf. When plants overwinter in the field under freezing temperatures and are then brought into the greenhouse during late winter to continue growth undisturbed by clipping under moderate temperatures (60–80 F.), culms are erect averaging 31.0 cm in length and 3.1 nodes per culm. The uppermost internode averages 7.6 cm in length. The peduncle average 20.7 cm in length and 0.76 mm in width. The vegetative leaf averages 19.3 cm in length, 3.0 mm in width, 0.30 mm in thickness and the ligule 0.14 mm in length. The flag leaf averages 4.3 cm in length, 3.1 mm in width, 0.20 mm in thickness and a ligule length of 1.2 mm.

The panicle averages 75.1 mm in length, 53.4 mm in width, and 9.8 whorls. The lowest whorl and the third whorl from the bottom of the panicle average 3.9 and 3.6 branches, respectively. A spikelet in the lowest whorl averages 4.2 mm in length, 2.1 mm in width, 2.4 florets, the outer and inner glumes average 2.5 mm and 2.9 mm in length, respectively. A spikelet from the third whorl from the bottom of the panicle averages 4.4 mm in length, 2.2 mm in width, 2.1 florets and the outer and inner glumes average 2.5 mm and 2.9 mm in length, respectively.

Conditioned seed of Ba74-17 averages 3.00 mm in length, 0.88 mm in width, a rachilla length of 0.83 mm and an average hair content at the base of the lemma.

Comparisons of Ba74-17 with other Kentucky Bluegrass varieties in terms of seed dimensions and seed numbers per pound are shown in Tables 1 and 2 as follows:

TABLE 1

Morphological Comparisons of Seed Length and Width; Rachilla and Lemma Hairs of Ba74-17 and Other Kentucky Bluegrass Varieties After Conditioning at Marysville, OH.

| | Seed | | | |
|---|---|---|---|---|
| Variety | Length mm | Width mm | Rachilla mm | Lemma Hairs* |
| Ba74-17 | 3.00 | 0.88 | 0.83 | 4.4 |
| Abbey | 2.97 | 0.89 | 0.80 | 3.8 |
| Adelphi | 2.70 | 0.84 | 0.65 | 4.4 |

TABLE 1-continued

Morphological Comparisons of Seed Length and Width; Rachilla and Lemma Hairs of Ba74-17 and Other Kentucky Bluegrass Varieties After Conditioning at Marysville, OH.

| | Seed | | | |
|---|---|---|---|---|
| Variety | Length mm | Width mm | Rachilla mm | Lemma Hairs* |
| Allure | 2.78 | 0.86 | 0.70 | 4.7 |
| Ascot | 3.00 | 0.85 | 0.82 | 3.9 |
| Baron | 3.08 | 0.81 | 0.71 | 5.0 |
| Bristol | 2.94 | 0.88 | 0.73 | 4.3 |
| Buckingham | 3.23 | 0.89 | 0.88 | 4.2 |
| Cannon | 3.00 | 0.94 | 0.86 | 4.9 |
| Chateau | 2.81 | 0.86 | 0.71 | 4.5 |
| Coventry | 2.71 | 0.81 | 0.70 | 4.0 |
| Eclipse | 2.77 | 0.83 | 0.68 | 3.5 |
| Georgetown | 2.94 | 0.82 | 0.74 | 4.9 |
| Gnome | 2.78 | 0.83 | 0.75 | 4.1 |
| Kelly | 3.07 | 0.89 | 0.75 | 4.2 |
| Midnight | 2.94 | 0.76 | 0.78 | 5.7 |
| Nassau | 3.07 | 0.86 | 0.68 | 3.4 |
| Nottingham | 3.05 | 0.88 | 0.82 | 3.8 |
| Ram 1 | 3.23 | 0.89 | 0.80 | 6.0 |
| Touchdown | 2.93 | 0.88 | 0.41 | 4.6 |
| Victa | 3.00 | 0.80 | 0.82 | 3.5 |
| Viva | 3.04 | 0.91 | 0.84 | 4.4 |
| LSD (.05) | 0.16 | 0.05 | 0.13 | 0.86 |

*Rating Scale: 0–9; 9 = most hairs

TABLE 2

Comparisons of Seeds Per Pound of Ba74-17 and Other Kentucky Bluegrass Varieties After Conditioning.

| Variety | Seeds Per Pound |
|---|---|
| Ba74-17 | 1,128,600 |
| Ba78-258 | 1,127,000 |
| Ba78-165 | 965,500 |
| Abbey | 988,500 |
| Buckingham | 978,000 |
| Cannon | 1,023,250 |
| Coventry | 1,374,750 |
| Garfield | 1,250,500 |
| Newport | 1,250,250 |
| Viva | 993,500 |
| LSD (.05) | 77,042 |

Ba74-17 differs significantly from several of the other Kentucky Bluegrass varieties in regard to the following morphological characteristics: (1) the culm length and number of nodes per culm; (2) the number of florets in both the lowest and third whorl; (3) the length of the outer glumes in the third whorl; and (4) vegetative leaf length, ligule length and leaf margin hairs. Since environmental conditions such as soil and climate may influence morphological characteristics to some extent comparisons of Ba74-17 were made with other Kentucky Bluegrass varieties and the comparisons are set forth in Tables 3–8:

TABLE 3

Morphological Comparison of Panicles, Whorl Number and Whorl Branches of Ba74-17 and Other Kentucky Bluegrass Varieties in the Greenhouse at Marysville, OH

| | Panicles | | | | Number of Branches | |
|---|---|---|---|---|---|---|
| Variety | Nodding* | Length (mm) | Width (mm) | Whorl Number | Lowest Whorl | Third Whorl |
| Ba74-17 | 1.3 | 75.1 | 53.4 | 9.8 | 3.9 | 3.6 |
| Abbey | 1.6 | 80.4 | 59.3 | 9.3 | 3.8 | 3.3 |
| Adelphi | 1.8 | 106.8 | 76.4 | 10.0 | 3.6 | 3.0 |
| Allure | 2.2 | 60.8 | 47.6 | 8.4 | 3.9 | 3.0 |
| Ascot | 2.4 | 77.1 | 66.0 | 9.2 | 2.3 | 2.1 |
| Baron | 2.2 | 92.6 | 71.0 | 10.0 | 3.4 | 2.8 |
| Bristol | 2.0 | 85.5 | 61.5 | 8.4 | 2.8 | 2.7 |
| Buckingham | 2.0 | 88.8 | 62.0 | 9.3 | 2.1 | 2.1 |
| Cannon | 1.1 | 80.2 | 55.3 | 9.8 | 4.1 | 3.9 |
| Chateau | 2.9 | 65.2 | 57.3 | 8.5 | 3.3 | 2.8 |
| Coventry | 2.5 | 64.0 | 54.2 | 8.4 | 3.3 | 2.5 |
| Eclipse | 1.3 | 89.2 | 74.0 | 10.7 | 3.3 | 2.1 |
| Georgetown | 1.0 | 80.0 | 57.0 | 7.4 | 2.1 | 2.6 |
| Gnome | 1.1 | 80.6 | 56.0 | 10.6 | 4.6 | 3.9 |
| Kelly | 2.0 | 88.0 | 70.2 | 9.8 | 4.6 | 3.7 |
| Midnight | 2.0 | 75.8 | 48.4 | 7.1 | 2.9 | 3.0 |
| Nassau | 2.2 | 91.2 | 68.6 | 10.0 | 2.5 | 2.1 |
| Nottingham | 1.2 | 77.5 | 56.1 | 8.7 | 4.0 | 3.5 |
| Ram 1 | 1.3 | 67.7 | 47.0 | 7.3 | 3.0 | 3.2 |
| Touchdown | 1.1 | 73.1 | 75.0 | 7.6 | 2.1 | 2.3 |
| Victa | 1.7 | 74.9 | 58.3 | 10.0 | 4.7 | 3.5 |
| Viva | 1.6 | 88.8 | 68.4 | 8.8 | 4.3 | 3.7 |
| LSD (.05) | 0.68 | 7.35 | 8.62 | 0.66 | 0.72 | 0.50 |

*Rating Scale: 1–9; 9 = most nodding

TABLE 4

Morphological Comparison of Spikelets and Florets of Ba74-17 and Other Kentucky Bluegrass Varieties in the Greenhouse at Marysville, OH.

| | Spikelets | | | | Number of Florets | |
|---|---|---|---|---|---|---|
| | Lowest Whorl | | Third Whorl | | Per Spikelet | |
| Variety | Length mm | Width mm | Length mm | Width mm | Lowest Whorl | Third Whorl |
| Ba74-17 | 4.2 | 2.1 | 4.4 | 2.2 | 2.4 | 2.1 |
| Abbey | 4.4 | 2.2 | 4.5 | 2.2 | 3.0 | 3.0 |
| Adelphi | 4.6 | 2.2 | 4.8 | 2.2 | 4.4 | 4.4 |
| Allure | 4.3 | 2.2 | 4.3 | 2.2 | 3.4 | 3.2 |
| Ascot | 5.4 | 2.6 | 5.3 | 2.9 | 3.1 | 3.1 |
| Baron | 5.4 | 2.8 | 5.4 | 3.1 | 4.0 | 4.2 |
| Bristol | 4.9 | 2.4 | 5.0 | 2.5 | 4.2 | 4.5 |
| Buckingham | 5.6 | 3.2 | 5.6 | 3.3 | 4.1 | 4.1 |
| Cannon | 4.7 | 2.4 | 4.6 | 2.6 | 2.7 | 2.7 |
| Chateau | 4.4 | 2.4 | 4.4 | 2.4 | 3.4 | 3.5 |
| Coventry | 4.4 | 2.2 | 4.5 | 2.4 | 3.2 | 3.5 |
| Eclipse | 4.6 | 2.4 | 4.6 | 2.4 | 3.6 | 3.6 |
| Georgetown | 5.0 | 2.3 | 5.0 | 2.6 | 4.8 | 4.9 |
| Gnome | 4.6 | 2.5 | 4.6 | 2.9 | 3.2 | 3.2 |
| Kelly | 5.1 | 2.5 | 5.2 | 2.8 | 3.7 | 3.8 |
| Midnight | 5.3 | 2.5 | 5.5 | 2.4 | 4.4 | 4.7 |
| Nassau | 4.7 | 2.6 | 4.8 | 3.0 | 4.2 | 4.3 |
| Nottingham | 4.6 | 2.5 | 4.8 | 2.6 | 3.3 | 3.4 |
| Ram 1 | 5.4 | 2.6 | 5.3 | 2.8 | 3.6 | 3.4 |
| Touchdown | 5.1 | 2.9 | 4.8 | 2.8 | 4.1 | 4.0 |
| Victa | 4.5 | 2.5 | 4.5 | 2.4 | 3.3 | 3.2 |
| Viva | 4.6 | 2.5 | 4.7 | 2.6 | 2.6 | 2.8 |
| LSD (.05) | 0.41 | 0.35 | 0.38 | 0.35 | 0.58 | 0.3 |

TABLE 5

Morphological Comparison of Glumes of Ba74-17 and Other Kentucky Bluegrass Varieties in the Greenhouse at Marysville, OH

| | Glume Length (mm) | | | |
|---|---|---|---|---|
| | Outer | | Inner | |
| Variety | Lowest Whorl | Third Whorl | Lowest Whorl | Third Whorl |
| Ba74-17 | 2.5 | 2.5 | 2.9 | 2.9 |
| Abbey | 2.7 | 2.7 | 3.1 | 3.1 |
| Adelphi | 2.7 | 2.6 | 3.0 | 3.1 |
| Allure | 2.6 | 2.7 | 3.0 | 3.0 |
| Ascot | 3.7 | 3.7 | 4.1 | 4.0 |
| Baron | 3.1 | 3.2 | 3.6 | 3.7 |
| Bristol | 2.8 | 3.0 | 3.3 | 3.4 |
| Buckingham | 3.5 | 3.3 | 3.9 | 3.8 |
| Cannon | 2.8 | 2.9 | 3.2 | 3.1 |
| Chateau | 2.8 | 2.9 | 3.1 | 3.2 |
| Coventry | 2.7 | 2.8 | 3.1 | 3.1 |
| Eclipse | 3.0 | 3.0 | 3.4 | 3.4 |
| Georgetown | 2.8 | 2.8 | 3.1 | 3.1 |
| Gnome | 2.8 | 2.9 | 3.3 | 3.3 |
| Kelly | 3.0 | 3.1 | 3.4 | 3.5 |
| Midnight | 2.6 | 2.6 | 3.0 | 3.1 |
| Nassau | 2.6 | 2.7 | 2.9 | 3.0 |
| Nottingham | 2.7 | 2.8 | 3.3 | 3.3 |
| Ram 1 | 2.9 | 3.0 | 3.6 | 3.5 |
| Touchdown | 3.3 | 3.3 | 3.8 | 3.8 |
| Victa | 2.8 | 2.7 | 3.1 | 3.1 |
| Viva | 2.8 | 2.8 | 3.2 | 3.1 |
| LSD (.05) | 0.23 | 0.22 | 0.22 | 0.23 |

| | Glume Hairs* | | | |
|---|---|---|---|---|
| | Lowest Whorl | | Third Whorl | |
| Variety | Outer | Inner | Outer | Inner |
| Ba74-17 | 1.3 | 3.0 | 1.9 | 2.9 |
| Abbey | 0.6 | 0.9 | 1.0 | 1.0 |
| Adelphi | 0.6 | 2.7 | 1.1 | 1.9 |
| Allure | 2.5 | 3.0 | 2.5 | 2.5 |
| Ascot | 2.1 | 3.0 | 2.0 | 2.3 |
| Baron | 4.8 | 4.4 | 4.2 | 4.6 |
| Bristol | 1.0 | 2.2 | 0.8 | 2.2 |
| Buckingham | 2.6 | 3.2 | 2.2 | 2.8 |
| Cannon | 1.7 | 2.3 | 2.1 | 2.3 |
| Chateau | 1.5 | 2.6 | 2.0 | 1.8 |
| Coventry | 1.5 | 2.7 | 1.6 | 2.4 |
| Eclipse | 1.5 | 1.9 | 1.8 | 1.9 |
| Georgetown | 1.7 | 2.7 | 1.2 | 2.4 |
| Gnome | 1.0 | 1.9 | 1.2 | 1.6 |
| Kelly | 1.3 | 1.5 | 1.1 | 0.8 |
| Midnight | 1.8 | 2.8 | 1.0 | 2.4 |
| Nassau | 2.1 | 2.6 | 4.2 | 4.4 |
| Nottingham | 2.4 | 2.2 | 1.9 | 2.1 |
| Ram 1 | 1.1 | 2.3 | 0.7 | 1.2 |
| Touchdown | 0.7 | 2.1 | 1.1 | 1.4 |
| Victa | 0.8 | 1.1 | 1.1 | 1.3 |
| Viva | 1.7 | 1.3 | 1.3 | 2.0 |
| LSD (.05) | 0.9 | 0.9 | 0.9 | 0.9 |

*Rating Scale: 0–9; 9 = most hairs

TABLE 6

Morphological Comparison of Flag Leaves of Ba74-17 and Other Kentucky Bluegrass Varieties in the Greenhouse at Marysville, OH

| | Leaves | | | | |
|---|---|---|---|---|---|
| Variety | Length cm | Width mm | Thickness mm | Angle | Curve |
| Ba74-17 | 4.3 | 3.1 | 0.20 | 1.2 | 5.0 |
| Abbey | 3.8 | 3.4 | 0.14 | 2.7 | 4.1 |
| Adelphi | 5.7 | 3.4 | 0.18 | 5.2 | 5.0 |
| Allure | 3.8 | 2.9 | 0.21 | 1.0 | 4.9 |
| Ascot | 4.7 | 3.5 | 0.29 | 2.1 | 4.5 |
| Baron | 7.0 | 4.2 | 0.15 | 9.2 | 4.4 |
| Bristol | 4.3 | 3.2 | 0.21 | 2.3 | 5.0 |
| Buckingham | 5.3 | 3.4 | 0.23 | 1.4 | 5.0 |
| Cannon | 4.3 | 3.5 | 0.22 | 1.9 | 5.0 |
| Chateau | 4.0 | 2.7 | 0.19 | 3.4 | 2.0 |
| Coventry | 3.7 | 3.0 | 0.14 | 0.7 | 4.3 |
| Eclipse | 3.9 | 3.2 | 0.19 | 8.7 | 5.0 |
| Georgetown | 5.7 | 2.8 | 0.22 | 1.9 | 5.0 |
| Gnome | 4.5 | 3.5 | 0.18 | 4.3 | 5.0 |
| Kelly | 4.8 | 4.1 | 0.18 | 3.1 | 4.4 |
| Midnight | 3.8 | 2.6 | 0.19 | 1.1 | 5.0 |
| Nassau | 6.0 | 3.7 | 0.19 | 5.9 | 4.7 |
| Nottingham | 4.3 | 3.7 | 0.22 | 2.0 | 4.6 |
| Ram 1 | 3.4 | 3.1 | 0.19 | 1.0 | 4.8 |
| Touchdown | 4.1 | 2.7 | 0.16 | 3.4 | 4.1 |
| Victa | 3.9 | 3.7 | 0.27 | 2.1 | 4.6 |
| Viva | 4.5 | 3.6 | 0.18 | 5.1 | 4.4 |
| LSD (.05) | 1.0 | 0.42 | 0.02 | 2.50 | 0.44 |

| | Hairs* | | | |
|---|---|---|---|---|
| Variety | Ligule mm | Leaf Margin | Ligule | Sheath Color** |
| Ba74-17 | 1.2 | 0.2 | 2.8 | 2.0 |
| Abbey | 1.3 | 0.8 | 1.6 | 0.2 |
| Adelphi | 1.1 | 1.8 | 1.6 | 0.4 |
| Allure | 0.8 | 0.4 | 2.3 | 2.0 |
| Ascot | 1.5 | 0.6 | 0.7 | 0.9 |
| Baron | 1.2 | 1.0 | 3.8 | 2.6 |
| Bristol | 0.6 | 0.4 | 1.9 | 2.0 |
| Buckingham | 1.2 | 0.5 | 2.1 | 1.8 |
| Cannon | 1.3 | 0.4 | 3.6 | 1.5 |
| Chateau | 0.9 | 1.1 | 3.1 | 0.3 |
| Coventry | 0.9 | 0.8 | 1.7 | 2.0 |
| Eclipse | 1.1 | 1.0 | 1.0 | 0.2 |
| Georgetown | 0.6 | 0.6 | 2.0 | 2.0 |
| Gnome | 0.8 | 0.9 | 3.2 | 1.5 |
| Kelly | 1.5 | 1.1 | 2.5 | 2.2 |
| Midnight | 30.4 | 0.4 | 0.3 | 2.0 |
| Nassau | 1.1 | 2.6 | 2.4 | 0.8 |
| Nottingham | 1.3 | 1.5 | 2.3 | 1.8 |
| Ram 1 | 0.7 | 0.5 | 1.3 | 2.0 |
| Touchdown | 1.1 | 1.0 | 1.0 | 7.7 |
| Victa | 1.3 | 1.0 | 0.8 | 0.5 |
| Viva | 1.5 | 0.4 | 2.2 | 0.5 |
| LSD (.05) | 0.17 | 0.50 | 0.70 | 0.76 |

*Rating Scale: 0–9; 9 = most hairs
**Rating Scale: 0–9; 9 = most color

TABLE 7

Morphological Comparison of Peduncles, Culms, Nodes Per Culm and Top Internode Length of Ba74-17 and Other Kentucky Bluegrass Varieties in the Greenhouse at Marysville, OH

| | Peduncle | | Culm | | Top |
|---|---|---|---|---|---|
| Variety | Length cm | Width mm | Length cm | Nodes Per Culm | Internode length (cm) |
| Ba74-17 | 20.7 | 0.76 | 31.0 | 3.1 | 7.6 |
| Abbey | 23.2 | 0.65 | 41.3 | 4.1 | 11.0 |

TABLE 7-continued

Morphological Comparison of Peduncles, Culms, Nodes Per Culm and Top Internode Length of Ba74-17 and Other Kentucky Bluegrass Varieties in the Greenhouse at Marysville, OH

| | Peduncle | | Culm | | Top |
|---|---|---|---|---|---|
| Variety | Length cm | Width mm | Length cm | Nodes Per Culm | Internode length (cm) |
| Adelphi | 24.5 | 0.66 | 40.0 | 4.0 | 10.4 |
| Allure | 17.9 | 0.61 | 28.0 | 3.1 | 7.7 |
| Ascot | 20.0 | 0.64 | 36.3 | 3.0 | 12.7 |
| Baron | 34.0 | 0.70 | 52.8 | 4.2 | 12.8 |
| Bristol | 22.9 | 0.73 | 43.5 | 4.0 | 12.6 |
| Buckingham | 24.7 | 0.71 | 44.9 | 3.7 | 13.4 |
| Cannon | 24.3 | 0.81 | 39.5 | 3.1 | 10.8 |
| Chateau | 20.7 | 0.61 | 38.9 | 4.4 | 9.9 |
| Coventry | 19.6 | 0.49 | 34.7 | 4.5 | 7.9 |
| Eclipse | 23.7 | 0.66 | 39.2 | 4.9 | 9.9 |
| Georgetown | 21.7 | 0.68 | 37.5 | 3.2 | 11.1 |
| Gnome | 19.4 | 0.84 | 35.3 | 3.1 | 9.2 |
| Kelly | 29.4 | 0.75 | 46.6 | 3.6 | 11.8 |
| Midnight | 20.5 | 0.72 | 29.5 | 2.8 | 7.6 |
| Nassau | 25.0 | 0.66 | 36.0 | 3.9 | 7.4 |
| Nottingham | 26.9 | 0.82 | 39.7 | 2.9 | 9.7 |
| Ram 1 | 22.2 | 0.69 | 30.5 | 2.5 | 6.6 |
| Touchdown | 23.6 | 0.52 | 38.0 | 4.0 | 8.4 |
| Victa | 21.2 | 0.81 | 37.9 | 3.7 | 10.3 |
| Viva | 26.4 | 0.70 | 42.7 | 4.1 | 9.2 |
| LSD (.05) | 3.2 | 0.08 | 3.3 | 0.4 | 1.9 |

TABLE 8

Morphological Comparison of Vegetative Leaves of Ba74-17 and Other Kentucky Bluegrass Varieties in the Greenhouse at Marysville, OH

| | Leaf | | | | |
|---|---|---|---|---|---|
| Variety | Length cm | Width mm | Thickness mm | Angle* | Curve*** |
| Ba74-17 | 19.3 | 3.0 | 0.30 | 51.9 | 7.3 |
| Abbey | 20.7 | 3.6 | 0.28 | 51.3 | 7.4 |
| Adelphi | 19.4 | 3.7 | 0.28 | 67.0 | 4.6 |
| Allure | 18.1 | 3.5 | 0.30 | 53.0 | 6.2 |
| Ascot | 17.4 | 3.4 | 0.35 | 67.9 | 5.5 |
| Baron | 18.2 | 4.3 | 0.29 | 35.0 | 4.4 |
| Bristol | 18.2 | 3.7 | 0.32 | 65.5 | 6.9 |
| Buckingham | 18.9 | 4.5 | 0.36 | 50.9 | 5.0 |
| Cannon | 22.1 | 3.3 | 0.30 | 62.5 | 8.2 |
| Chateau | 23.1 | 3.3 | 0.33 | 39.7 | 5.4 |
| Coventry | 23.4 | 3.6 | 0.25 | 63.0 | 7.3 |
| Eclipse | 20.3 | 4.4 | 0.30 | 65.5 | 5.4 |
| Georgetown | 19.5 | 3.6 | 0.29 | 56.7 | 5.8 |
| Gnome | 18.2 | 2.9 | 0.29 | 43.2 | 6.6 |
| Kelly | 22.8 | 3.9 | 0.30 | 55.5 | 7.0 |
| Midnight | 19.5 | 3.5 | 0.31 | 63.3 | 5.0 |
| Nassau | 16.3 | 3.7 | 0.29 | 63.2 | 4.9 |
| Nottingham | 18.6 | 3.8 | 0.34 | 61.6 | 7.7 |
| Ram 1 | 19.1 | 3.6 | 0.27 | 70.8 | 6.5 |
| Touchdown | 16.7 | 3.7 | 0.24 | 51.3 | 4.0 |
| Victa | 21.5 | 3.6 | 0.36 | 56.3 | 6.7 |
| Viva | 22.9 | 3.8 | 0.40 | 53.0 | 7.1 |
| LSD (.05) | 3.5 | 0.43 | 0.04 | 15.9 | 1.5 |

| | Ligule | Hairs*** | | |
|---|---|---|---|---|
| | Length | Leaf | Leaf | Color*** |
| Ba74-17 | 0.14 | 3.5 | 0.9 | 2.0 |
| Abbey | 0.32 | 4.4 | 2.8 | 0.0 |
| Adelphi | 0.34 | 2.6 | 3.4 | 0.0 |
| Allure | 0.14 | 2.0 | 1.6 | 1.9 |
| Ascot | 0.22 | 1.5 | 2.0 | 1.4 |
| Baron | 0.33 | 4.6 | 3.6 | 0.4 |
| Bristol | 0.12 | 2.6 | 3.0 | 2.0 |

TABLE 8-continued

Morphological Comparison of Vegetative Leaves of Ba74-17 and Other Kentucky Bluegrass Varieties in the Greenhouse at Marysville, OH

| | | | | |
|---|---|---|---|---|
| Buckingham | 0.14 | 3.3 | 2.6 | 2.0 |
| Cannon | 0.16 | 3.2 | 0.7 | 2.0 |
| Chateau | 0.22 | 3.3 | 3.1 | 0.5 |
| Coventry | 0.32 | 3.1 | 2.4 | 0.3 |
| Eclipse | 0.38 | 2.8 | 2.6 | 0.2 |
| Georgetown | 0.14 | 2.5 | 2.4 | 2.0 |
| Gnome | 0.23 | 1.6 | 0.8 | 1.4 |
| Kelly | 0.34 | 4.6 | 2.4 | 0.0 |
| Midnight | 0.10 | 1.3 | 1.6 | 2.0 |
| Nassau | 0.34 | 2.5 | 3.3 | 1.4 |
| Nottingham | 0.21 | 3.1 | 2.0 | 1.4 |
| Ram 1 | 0.09 | 1.8 | 1.0 | 2.0 |
| Touchdown | 0.29 | 1.4 | 1.3 | 8.0 |
| Victa | 0.26 | 2.3 | 1.7 | 0.1 |
| Viva | 0.23 | 5.2 | 4.2 | 0.0 |
| LSD (.05) | 0.04 | 0.8 | 0.6 | 0.6 |

*Leaf Angle: Degrees from stem
**Leaf Curve: 1–9; 1–4 = curves up; 5 = no curve; 6–9 = curves down
***Leaf Hairs: 0–9; 0 = none; 9 = many
****Sheath Color: 0–9; 0 = none; 9 = many With regard to comparative analysis conducted for purposes of determining color of Ba74-17 plants relative to other Kentucky Bluegrass varieties, readings were taken of the vegetative color of Ba74-17 during mid-October while the turf was actively growing with adequate nutrient and water availability. The readings were taken in full sun with several actively growing leaves being compared, one at a time, utilizing color chips from the Munsell Book of Color as a reference. On this basis, the color of Ba74-17 was determined to be 5 GY 4/6. During the same time period, the color of similar leaves of other Kentucky Bluegrass varieties were determined by the same procedure to be as follows: Ascot—5 GY 4/4; Buckingham—7.5 GY 4/4; Ba77-700—5 GY 4/6; Midnight—7.5 GY 4/4; Abbey—5 GY 4/6; and and Victa—5 GY 4/4. However, it should be noted that the general apparent color of turf does not always correlate directly with the color of the individual actively growing leaves within the turf and that turf color varies with nutrient level and time of year with some varieties being darker or lighter green depending on such factors.

Comparisons of Ba74-17 with other Kentucky Bluegrass varieties for quality, genetic color, spring greenup, winter color, leaf texture, percent living ground, drought tolerance, canopy height, nitrogen deficiency, flood recovery and seedheads are set forth hereinafter in Tables 9–20.

TABLE 9

A Comparison of Quality of Ba74-17 and Other Kentucky Bluegrass Varieties under Low Maintenance in Five (5) Tests A–E conducted at various Locations in the US.

| | TESTS (Mean Values) | | | | |
|---|---|---|---|---|---|
| Variety | A | B | C | D | E |
| Ba74-17 | 5.3 | 4.9 | 4.4 | 4.6 | 3.9 |
| Baron | 5.3 | 5.0 | 4.5 | 4.6 | 4.1 |
| Gnome | 5.2 | 4.6 | 4.4 | 4.7 | 4.1 |
| Haga | 5.3 | 4.8 | 4.6 | 4.5 | 4.1 |
| Kenblue | 4.5 | 4.2 | 4.3 | 4.0 | 3.3 |
| Liberty | 5.2 | 5.0 | 4.5 | 4.4 | 3.9 |
| Merion | 4.3 | 4.6 | 4.2 | 4.5 | 3.9 |
| Merit | 5.4 | 4.9 | 4.5 | 4.6 | 4.1 |
| Midnight | 5.7 | 5.6 | 4.7 | 4.9 | 4.2 |
| Monopoly | 5.2 | 5.0 | 4.6 | 4.9 | 4.0 |
| Park | 4.6 | 4.2 | 4.1 | 4.1 | 3.8 |
| Ram 1 | 5.5 | 5.1 | 4.7 | 4.9 | 4.6 |

TABLE 9-continued

A Comparison of Quality of Ba74-17 and Other Kentucky Bluegrass Varieties under Low Maintenance in Five (5) Tests A–E conducted at various Locations in the US.

| | TESTS (Mean Values) | | | | |
|---|---|---|---|---|---|
| Variety | A | B | C | D | E |
| South Dakota | 4.1 | 3.9 | 3.9 | 3.9 | 3.3 |
| LSD (0.05) | 0.3 | 0.3 | 0.3 | 0.3 | 0.4 |

Rating Scale: 1–9; 9 = Ideal Turf

TABLE 10

A Comparison of Quality of Ba74-17 and Other Kentucky Bluegrass Varieties under Low Maintenance at Four (4) Locations in the US.

| | Test Locations | | | |
|---|---|---|---|---|
| Variety | Rathdrum Idaho | St. Louis Missouri | Pittstown New Jersey | Washington DC |
| Ba74-17 | 6.3 | 6.4 | 6.4 | 4.1 |
| Baron | 6.5 | 6.6 | 6.0 | 3.1 |
| Gnome | 6.1 | 6.3 | 5.7 | 3.1 |
| Haga | 6.7 | 6.0 | 5.1 | 3.2 |
| Kenblue | 4.5 | 5.1 | 3.7 | 3.2 |
| Liberty | 6.6 | 6.1 | 5.3 | 3.4 |
| Merion | 5.9 | 6.1 | 3.4 | 1.7 |
| Merit | 6.4 | 6.5 | 6.0 | 3.3 |
| Midnight | 7.2 | 7.8 | 6.7 | 2.4 |
| Monopoly | 4.9 | 5.5 | 4.8 | 3.9 |
| Park | 4.6 | 5.0 | 3.9 | 3.3 |
| Ram 1 | 7.1 | 6.9 | 6.2 | 2.8 |
| South Dakota | 4.0 | 4.5 | 3.5 | 2.3 |
| LSD (0.05) | 0.9 | 0.8 | 0.7 | 1.0 |

Rating Scale: 1–9; 9 = Ideal Turf

TABLE 11

A Comparison of Genetic Color of Ba74-17 and Other Kentucky Bluegrass Varieties under Low Maintenance at Seven (7) Locations in US.

| | Color Ratings By Locations | | | | | | |
|---|---|---|---|---|---|---|---|
| Variety | Rath-drum ID | St. Louis MO | Lincoln NE | North Brunswick NJ | Marys-ville OH | Univ. Park PA | Nor-ton VA |
| 74-17 | 7.2 | 6.7 | 6.4 | 7.0 | 7.2 | 6.4 | 6.3 |
| Baron | 6.0 | 6.9 | 6.4 | 6.3 | 7.5 | 6.3 | 6.5 |
| Gnome | 6.8 | 6.7 | 6.6 | 5.3 | 7.5 | 6.1 | 6.7 |
| Haga | 3.3 | 5.6 | 5.8 | 4.3 | 6.3 | 5.4 | 5.0 |
| Kenblue | 4.5 | 6.2 | 5.6 | 3.7 | 7.2 | 5.7 | 3.7 |
| Liberty | 6.0 | 6.6 | 6.0 | 5.3 | 7.0 | 5.8 | 5.7 |
| Merion | 5.7 | 6.3 | 5.8 | 5.3 | 7.0 | 5.8 | 5.0 |
| Merit | 6.5 | 6.6 | 6.4 | 5.7 | 7.2 | 6.2 | 6.7 |
| Midnight | 7.3 | 7.3 | 7.4 | 7.3 | 8.2 | 8.0 | 7.2 |
| Monopoly | 2.3 | 5.8 | 5.4 | 3.7 | 6.0 | 4.9 | 5.0 |
| Park | 4.0 | 5.3 | 5.3 | 3.0 | 6.5 | 4.9 | 4.0 |
| Ram 1 | 7.2 | 7.2 | 6.0 | 6.0 | 7.3 | 6.1 | 5.8 |
| South | 4.8 | 5.8 | 5.2 | 3.7 | 7.0 | 5.9 | 4.3 |
| LSD (0.05) | 1.6 | 1.0 | 0.7 | 1.2 | 0.5 | 0.9 | 0.9 |

Genetic Color Rating Scale: 1–9; 9 = Dark

TABLE 12

A Comparison of Spring Greenup Ba74-17 and Other Kentucky Bluegrass Varieties under Low Maintenance at Two (2) locations in the US.

| Variety | Univ. Park, PA | Rathdrum ID |
|---|---|---|
| Ba74-17 | 7.0 | 3.3 |
| Baron | 6.3 | 2.7 |
| Gnome | 6.0 | 3.0 |
| Haga | 5.3 | 2.3 |
| Kenblue | 2.7 | 1.3 |
| Liberty | 5.7 | 2.3 |
| Merion | 7.7 | 3.3 |
| Merit | 6.3 | 2.7 |
| Midnight | 8.3 | 2.3 |
| Monopoly | 2.7 | 1.7 |
| Park | 3.3 | 2.3 |
| Ram 1 | 7.0 | 1.0 |
| South Dakota | 3.0 | 1.3 |
| LSD (0.05) | 1.8 | 0.8 |

Spring Greenup Rating Scale: 1–9; 9 = Completely Green

TABLE 13

A Comparison of Winter Color of Ba74-17 and Other Kentucky Bluegrass Varieties under Low maintenance at Rathdrum, ID

| Variety | Winter Color |
|---|---|
| Ba74-17 | 7.0 |
| Baron | 6.3 |
| Gnome | 6.7 |
| Haga | 6.3 |
| Kenblue | 3.7 |
| Liberty | 6.7 |
| Merion | 7.7 |
| Merit | 7.0 |
| Midnight | 8.3 |
| Monopoly | 3.7 |
| Park | 5.3 |
| Ram 1 | 7.7 |
| South Dakota | 3.7 |
| LSD (0.05) | 1.5 |

Winter Color Rating Scale: 1–9; 9 = Complete Color Retention

TABLE 14

A Comparison of Leaf Texture of Ba74-17 and Other Kentucky Bluegrass Varieties under Low Maintenance at Two (2) Locations in the US.

| Variety | Rathdrum ID | St. Louis MO |
|---|---|---|
| Ba74-17 | 6.3 | 5.3 |
| Baron | 5.7 | 5.8 |
| Gnome | 6.0 | 5.3 |
| Haga | 6.7 | 6.2 |
| Kenblue | 9.0 | 7.8 |
| Liberty | 7.3 | 5.9 |
| Merion | 6.0 | 5.5 |
| Merit | 5.7 | 5.1 |
| Midnight | 8.3 | 6.3 |
| Monopoly | 6.3 | 5.8 |
| Park | 8.0 | 6.7 |
| Ram 1 | 7.3 | 6.4 |
| South Dakota | 8.3 | 6.8 |
| LSD (0.05) | 1.1 | 0.8 |

Leaf Texture Rating Scale: 1–9; 9 = very fine

TABLE 15

A Comparison of Percent Living Ground Cover in Spring of Ba74-17 and Other Kentucky Bluegrass Varieties under Low Maintenance at the Washington Monument Grounds, DC.

| Variety | % Cover |
|---|---|
| Ba74-17 | 41.7 |
| Baron | 25.0 |
| Gnome | 31.7 |
| Haga | 48.3 |
| Kenblue | 33.3 |
| Liberty | 43.3 |
| Merion | 10.0 |
| Merit | 20.0 |
| Midnight | 21.7 |
| Monopoly | 53.3 |
| Park | 33.3 |
| Ram 1 | 36.7 |
| South Dakota | 11.7 |
| LSD (0.05) | 23.2 |

TABLE 16

A Comparison of Drought Tolerance (Dormancy) of Ba74-17 and Other Kentucky Bluegrass Varieties under Low Maintenance at Beltsville, MD and Hubbard, OR.

| Variety | Beltsville MD | Hubbard OR |
|---|---|---|
| Ba74-17 | 6.3 | 5.3 |
| Baron | 4.7 | 2.0 |
| Gnome | 5.3 | 3.0 |
| Haga | 5.3 | 2.0 |
| Kenblue | 4.0 | 2.7 |
| Liberty | 3.0 | 3.0 |
| Merion | 6.0 | 4.7 |
| Merit | 5.7 | 4.0 |
| Midnight | 6.7 | 3.0 |
| Monopoly | 5.7 | 3.0 |
| Park | 4.7 | 3.3 |
| Ram 1 | 5.7 | 4.0 |
| South Dakota | 5.7 | 3.7 |
| LSD (0.05) | 2.0 | 2.2 |

Dormancy Rating Scale: 1–9; 9 = No Dormancy

TABLE 17

A Comparison of Canopy Height in Inches of Ba74-17 and Other Kentucky Bluegrass Varieties under Low Maintenance at University Park, PA.

| Variety | Height in Inches |
|---|---|
| Ba74-17 | 4.5 |
| Baron | 5.0 |
| Gnome | 5.2 |
| Haga | 6.2 |
| Kenblue | 7.3 |
| Liberty | 4.5 |
| Merion | 4.3 |
| Merit | 4.5 |
| Midnight | 3.2 |
| Monopoly | 7.0 |
| Park | 7.3 |
| Ram 1 | 5.2 |
| South Dakota | 6.3 |
| LSD (0.05) | 1.4 |

TABLE 18

A Comparison of Nitrogen Deficiency Ratings of Ba74-17 and Other Kentucky Bluegrass Varieties under Low Maintenance at Rathdrum, ID.

| Variety | Nitrogen Deficiency |
|---|---|
| Ba74-17 | 6.3 |
| Baron | 6.3 |
| Gnome | 6.7 |
| Haga | 5.0 |
| Kenblue | 1.7 |
| Liberty | 6.7 |
| Merion | 3.7 |
| Merit | 5.3 |
| Midnight | 7.0 |
| Monopoly | 5.3 |
| Park | 4.0 |
| Ram 1 | 7.3 |
| South Dakota | 1.7 |
| LSD (0.05) | 2.1 |

Nitrogen Deficiency Rating Scale: 1–9; 9 = no symptoms

TABLE 19

A Comparison of Flood Recovery Ratings of Ba74-17 and Other Kentucky Bluegrass Varieties under Low Maintenance at Lincoln, NE.

| Variety | Flood Recovery |
|---|---|
| Ba74-17 | 5.7 |
| Baron | 3.3 |
| Gnome | 4.0 |
| Haga | 1.7 |
| Kenblue | 2.3 |
| Liberty | 3.3 |
| Merion | 5.3 |
| Merit | 4.0 |
| Midnight | 4.3 |
| Monopoly | 1.7 |
| Park | 1.7 |
| Ram 1 | 2.3 |
| South Dakota | 2.0 |
| LSD (0.05) | 3.2 |

Flood Recovery Rating Scale: 1–9; 9 = best

TABLE 20

A Comparison of Seedheads of Ba74-17 and Other Kentucky Bluegrass Varieties under Low Maintenance at North Brunswick, NJ.

| Variety | Seedheads |
|---|---|
| Ba74-17 | 2.3 |
| Baron | 3.0 |
| Gnome | 3.7 |
| Haga | 4.7 |
| Kenblue | 9.0 |
| Liberty | 4.0 |
| Merion | 4.0 |
| Merit | 2.0 |
| Midnight | 9.0 |
| Monopoly | 6.0 |
| Park | 9.0 |
| Ram 1 | 6.3 |
| South Dakota | 8.7 |
| LSD (0.05) | 1.8 |

Seedhead Rating Scale: 1–9; 9 = none

Turf diseases are one of the major causes of inconsistent and poor turf performance. Ba74-17 has been found to have a medium to high level of resistance to the following diseases: (a) leaf spot and melting out caused by *Drechslera poae* formerly called *Helminthosporium vagans;* (b) diseases such as leaf rust caused by Puccinia spp; (c) Fusarium patch caused by Fusarium spp; and (d) red thread caused by *Laetisaria fuciformis.*

Compounds of disease incidence of Ba74-17 as compared with other Kentucky Bluegrass Varieties in regard to leaf spot, melting out, leaf rust, Fusarium patch and red thread are presented in Tables 21–26.

TABLE 21

A Comparison of Leaf Spot Incidence of Ba74-17 and Other Kentucky Bluegrass Varieties under Low Maintenance at Five (5) Locations in the US.

| Variety | N. Brunswick NJ | Pittstown NJ | Marysville OH | Beltsville MD | Norton VA |
|---|---|---|---|---|---|
| Ba74-17 | 4.7 | 5.7 | 6.0 | 4.0 | 5.7 |
| Baron | 4.7 | 5.3 | 6.7 | 4.0 | 4.0 |
| Gnome | 3.7 | 4.0 | 6.3 | 3.3 | 4.7 |
| Haga | 2.7 | 3.3 | 6.3 | 3.3 | 4.3 |
| Kenblue | 1.0 | 1.0 | 3.3 | 1.3 | 2.3 |
| Liberty | 4.7 | 4.7 | 7.3 | 3.7 | 5.7 |
| Merion | 5.7 | 6.3 | 6.0 | 3.3 | 6.0 |
| Merit | 4.3 | 4.7 | 6.7 | 4.3 | 5.0 |
| Midnight | 7.7 | 7.3 | 7.7 | 6.7 | 6.3 |
| Monopoly | 3.3 | 3.3 | 5.7 | 3.7 | 4.0 |
| Park | 2.0 | 2.7 | 4.0 | 2.0 | 3.7 |
| Ram 1 | 4.3 | 3.7 | 6.7 | 4.7 | 4.3 |
| South | 1.0 | 1.3 | 3.3 | 1.0 | 4.0 |
| LSD (0.05) | 1.4 | 1.5 | 1.0 | 1.2 | 1.7 |

Leaf Spot Rating Scale: 1–9; 9 = no disease

TABLE 22

A Comparison of Leaf Spot Incidence of Ba74-17 and Other Kentucky Bluegrass Varieties under Low Maintenance at Pittstown, NJ and Ithaca, NY

| Variety | Pittstown NJ | Ithaca NY |
|---|---|---|
| Ba74-17 | 5.7 | 9.0 |
| Baron | 5.3 | 9.0 |
| Gnome | 4.0 | 9.0 |
| Haga | 3.3 | 8.0 |
| Kenblue | 1.0 | 1.3 |
| Liberty | 4.7 | 8.3 |
| Merion | 6.3 | 8.0 |
| Merit | 4.7 | 7.3 |
| Midnight | 7.3 | 9.0 |
| Monopoly | 3.3 | 5.0 |
| Park | 2.7 | 2.3 |
| Ram 1 | 3.7 | 3.7 |
| South Dakota | 1.3 | 4.3 |
| LSD (0.05) | 1.5 | 2.7 |

Leaf Spot Rating Scale: 1–9; 9 = No Disease

TABLE 23

A Comparison of Melting Out Incidence of Ba74-17 and Other Kentucky Bluegrass Varieties under Low Maintenance at Rathdrum, ID.

| Variety | Melting Out |
|---|---|
| Ba74-17 | 6.0 |
| Baron | 7.0 |
| Gnome | 5.3 |
| Haga | 6.3 |
| Kenblue | 4.0 |
| Liberty | 6.3 |
| Merion | 6.0 |
| Merit | 6.7 |
| Midnight | 8.0 |

TABLE 23-continued

A Comparison of Melting Out Incidence of Ba74-17 and Other Kentucky Bluegrass Varieties under Low Maintenance at Rathdrum, ID.

| Variety | Melting Out |
|---|---|
| Monopoly | 5.0 |
| Park | 4.3 |
| Ram 1 | 8.0 |
| South Dakota | 4.0 |
| LSD (0.05) | 1.5 |

Melting Out Rating Scale: 1–9; 9 = No Damage

TABLE 24

A Comparison of Leaf Rust Incidence of Ba74-17 and Other Kentucky Bluegrass Varieties under Low Maintenance at Rathdrum, ID.

| Variety | Leaf Rust |
|---|---|
| Ba74-17 | 7.3 |
| Baron | 6.0 |
| Gnome | 8.0 |
| Haga | 5.7 |
| Kenblue | 4.3 |
| Liberty | 6.5 |
| Merion | 3.7 |
| Merit | 6.3 |
| Midnight | 5.7 |
| Monopoly | 3.0 |
| Park | 2.7 |
| Ram 1 | 7.7 |
| South Dakota | 3.7 |
| LSD (0.05) | 1.7 |

Leaf Rust Rating Scale: 1–9; 9 = No Disease

TABLE 25

A Comparison of Fusarium Patch Incidence of Ba74-17 and Other Kentucky Bluegrass Varieties under Low Maintenance at Rathdrum, ID.

| Variety | Fusarium Patch |
|---|---|
| Ba74-17 | 5.7 |
| Baron | 4.3 |
| Gnome | 6.0 |
| Haga | 4.7 |
| Kenblue | 2.3 |
| Liberty | 6.0 |
| Merion | 3.3 |
| Merit | 5.7 |
| Midnight | 4.7 |
| Monopoly | 3.3 |
| Park | 1.7 |
| Ram 1 | 6.0 |
| South Dakota | 2.7 |
| LSD (0.05) | 1.8 |

Fusarium Patch Rating Scale: 1–9; 9 = No Disease

TABLE 26

A Comparison of Red Thread Incidence of Ba74-17 and Other Kentucky Bluegrass Varieties under Low Maintenance at Kingston, RI and Marysville, OH.

| Variety | Kingston RI | Marysville OH |
|---|---|---|
| Ba74-17 | 7.0 | 8.0 |
| Baron | 7.0 | 7.7 |
| Gnome | 5.7 | 8.0 |

TABLE 26-continued

A Comparison of Red Thread Incidence of Ba74-17 and Other Kentucky Bluegrass Varieties under Low Maintenance at Kingston, RI and Marysville, OH.

| Variety | Kingston RI | Marysville OH |
|---|---|---|
| Haga | 6.3 | 8.0 |
| Kenblue | 3.7 | 4.7 |
| Liberty | 7.7 | 8.0 |
| Merion | 8.3 | 7.7 |
| Merit | 7.0 | 8.0 |
| Midnight | 6.3 | 7.7 |
| Monopoly | 6.0 | 7.7 |
| Park | 6.0 | 6.0 |
| Ram 1 | 7.3 | 7.3 |
| South Dakota | 6.7 | 7.7 |
| LSD (0.05) | 2.1 | 1.2 |

Red Thread Rating Scale: 1–9; 9 = no disease

Additional comparisons for mature plant height, vegetative growth versus seed heads, panicle length, days to heading, days to anthesis and seed yields are presented in Tables 27–32.

TABLE 27

A Comparison of Mature Plant Height of Ba74-17 and Other Kentucky Bluegrass Varieties at Gervais, OR.

| Variety | Height cm |
|---|---|
| Ba74-17 | 62.2 |
| Ba78-258 | 60.3 |
| Ba77-700 | 60.0 |
| Ba78-165 | 53.4 |
| Abbey | 65.0 |
| Allure | 53.0 |
| Ascot | 56.0 |
| Bristol | 69.4 |
| Buckingham | 66.8 |
| Cannon | 68.4 |
| Chateau | 60.2 |
| Coventry | 62.4 |
| Estate | 57.4 |
| Fairfax | 60.6 |
| Gnome | 60.8 |
| Kelly | 65.2 |
| Newport | 74.9 |
| Victa | 68.2 |
| Viva | 61.6 |
| LSD (0.05) | 8.7 |

TABLE 28

A Comparison of Vegetative Growth Versus Seed Heads of Ba74-17 and Other Kentucky Bluegrass Varieties at Gervais, OR.

| Variety | Vegatative Growth vs Seed Heads |
|---|---|
| Ba74-17 | 5.6 |
| Ba78-258 | 6.9 |
| Ba77-700 | 7.2 |
| Ba78-165 | 5.8 |
| Abbey | 5.8 |
| Allure | 7.2 |
| Ascot | 4.2 |
| Bristol | 6.0 |
| Buckingham | 5.6 |
| Cannon | 8.0 |
| Chateau | 6.8 |
| Coventry | 8.0 |
| Estate | 8.6 |
| Fairfax | 7.2 |
| Gnome | 6.6 |

TABLE 28-continued

A Comparison of Vegetative Growth Versus Seed Heads of Ba74-17 and Other Kentucky Bluegrass Varieties at Gervais, OR.

| Variety | Vegatative Growth vs Seed Heads |
|---|---|
| Kelly | 4.8 |
| Newport | 3.4 |
| Victa | 7.8 |
| Viva | 7.2 |
| LSD (0.05) | 1.8 |

Vegetative Growth versus Seed Heads Rating Scale: 1–9; 9 = Most Vegetative Growth

TABLE 29

A Comparison of Panicle Length of Ba74-17 and Other Kentucky Bluegrass Varieties at Gervais, OR.

| Variety | Panicle Length (cm) |
|---|---|
| Ba74-17 | 9.3 |
| Ba78-258 | 11.1 |
| Ba77-700 | 8.9 |
| Ba78-165 | 8.6 |
| Abbey | 10.4 |
| Allure | 7.8 |
| Ascot | 9.5 |
| Bristol | 13.6 |
| Buckingham | 11.9 |
| Cannon | 9.9 |
| Chateau | 7.7 |
| Coventry | 7.8 |
| Estate | 8.3 |
| Fairfax | 9.1 |
| Gnome | 9.7 |
| Kelly | 9.7 |
| Newport | 10.8 |
| Victa | 10.0 |
| Viva | 9.8 |
| LSD (0.05) | 2.0 |

TABLE 30

A Comparison of Days to Heading of Ba74-17 and Other Kentucky Bluegrass Varieties at Gervais, OR.

| | Days to Heading | | |
|---|---|---|---|
| Variety | First | 50% | 100% |
| Ba74-17 | 103.0 | 119.2 | 122.0 |
| Ba78-258 | 110.1 | 125.5 | 128.1 |
| Ba77-700 | 109.8 | 125.4 | 127.2 |
| Ba78-165 | 100.2 | 118.6 | 121.6 |
| Abbey | 108.2 | 124.2 | 127.2 |
| Allure | 110.6 | 125.0 | 126.2 |
| Ascot | 88.0 | 112.0 | 118.6 |
| Bristol | 95.4 | 118.6 | 122.2 |
| Buckingham | 94.0 | 112.4 | 120.0 |
| Cannon | 113.4 | 125.0 | 127.0 |
| Chateau | 106.0 | 123.8 | 126.0 |
| Coventry | 105.8 | 122.4 | 124.6 |
| Estate | 105.8 | 123.8 | 125.6 |
| Fairfax | 102.6 | 121.6 | 124.4 |
| Gnome | 109.8 | 125.4 | 127.2 |

TABLE 30-continued

A Comparison of Days to Heading of Ba74-17 and Other Kentucky Bluegrass Varieties at Gervais, OR.

| | Days to Heading | | |
|---|---|---|---|
| Variety | First | 50% | 100% |
| Kelly | 112.2 | 125.4 | 127.2 |
| Newport | 85.0 | 109.8 | 118.2 |
| Victa | 111.6 | 125.0 | 127.0 |
| Viva | 109.4 | 125.0 | 127.2 |
| LSD (0.05) | 5.3 | 4.0 | 1.8 |

TABLE 31

A Comparison of Days to Anthesis of Ba74-17 and Other Kentucky Bluegrass Varieties at Gervais, OR.

| | Days to Anthesis | | |
|---|---|---|---|
| Variety | First | 50% | 100% |
| Ba74-17 | 125.0 | 127.0 | 132.0 |
| Ba78-258 | 129.1 | 134.1 | 137.5 |
| Ba77-700 | 129.0 | 134.4 | 137.8 |
| Ba78-165 | 124.2 | 126.2 | 132.0 |
| Abbey | 129.2 | 132.4 | 136.6 |
| Allure | 127.8 | 131.0 | 134.8 |
| Ascot | 118.6 | 123.8 | 131.8 |
| Bristol | 124.6 | 126.6 | 132.0 |
| Buckingham | 123.4 | 127.6 | 133.6 |
| Cannon | 129.0 | 132.2 | 136.0 |
| Chateau | 128.2 | 130.8 | 135.2 |
| Coventry | 126.6 | 128.6 | 134.4 |
| Estate | 127.0 | 129.2 | 135.2 |
| Fairfax | 125.8 | 128.8 | 132.8 |
| Gnome | 129.0 | 133.2 | 136.6 |
| Kelly | 129.0 | 132.8 | 136.6 |
| Newport | 120.4 | 123.4 | 131.4 |
| Victa | 129.0 | 132.2 | 136.0 |
| Viva | 129.0 | 132.8 | 136.6 |
| LSD (0.05) | 2.1 | 2.5 | 1.8 |

TABLE 32

A Comparison of Seed Yields of Ba74-17 and Other Kentucky Bluegrass Varieties in Three (3) Tests Conducted at Imbler, OR.

| | Seed Yield (Lb./acre) | | |
|---|---|---|---|
| Variety | Test 1 | Test 2 | Test 3 |
| Ba74-17 | 1,433 | 1,238 | 1,284 |
| Ba78-258 | 1,377 | 1,211 | 1,076 |
| Ba77-700 | 1,569 | 1,105 | 1,156 |
| Abbey | 1,549 | 1,324 | 1,090 |
| Buckingham | 748 | 923 | 740 |
| Cannon | 1,551 | 1,130 | 1,171 |
| Coventry | 1,046 | 839 | 847 |
| Fairfax | 1,159 | 1,074 | 766 |
| Viva | 1,612 | 1,111 | 1,054 |
| LSD (0.05) | 160 | 271 | 296 |

What is claimed is:

1. A variety of Kentucky Bluegrass, substantially as shown and described, characterized by a medium to high level of resistance to a broad spectrum of serious diseases including leaf spot and melting out, leaf rust, Fusarium patch and red thread; a dark green color throughout the growing season; a medium to high quality turf formation under a wide variety of environmental conditions; short growth and a high level of seed yielding capacity.

* * * * *

UNITED STATES PATENT AND TRADEMARK OFFICE

CERTIFICATE OF CORRECTION

PATENT NO. : PP 10,925
DATED : May 25, 1999
INVENTOR(S) : Virgil D. Meier et al.

It is certified that error appears in the above-identified patent and that said Letters Patent is hereby corrected as shown below:

Column 1,
Line 8, change "Bluegrass" to -- Bluegrasses --.

Column 7,
Table 6, under the heading "Ligule mm" for "Midnight Variety" change "30.4" to -- 0.4 --.

Column 8,
Table 8, change the heading "Ligule Length" to -- Ligule Length mm --; change the heading "Leaf" to -- Leaf Ligule --; change the heading "Leaf" (second occurrence) to -- Leaf Margin --; change the heading "Color*" to -- Sheath Color* --.

Column 9,
The first paragraph before Table 9, line 14, delete "and" (second occurrence).

Column 11,
Table 12, the heading "Rathdrum, ID" should appear above the first column of numbers and the heading "Univ. Park, PA" should appear above the second column of numbers.

Signed and Sealed this

Twenty-seventh Day of January, 2004

JON W. DUDAS
*Acting Director of the United States Patent and Trademark Office*